United States Patent [19]

Osakada

[11] Patent Number: 5,229,837
[45] Date of Patent: Jul. 20, 1993

[54] METHOD FOR DISTINGUISHING BETWEEN RECOVERED CONTAINERS FOR THE PRESENCE OR ABSENCE OF CONTAMINANTS

[75] Inventor: Kunio Osakada, Kawasaki, Japan
[73] Assignee: The Coca-Cola Company, Atlanta, Ga.
[21] Appl. No.: 720,477
[22] PCT Filed: Jan. 19, 1990
[86] PCT No.: PCT/JP90/00059
    § 371 Date: Jul. 9, 1991
    § 102(e) Date: Jul. 9, 1991
[87] PCT Pub. No.: WO90/07990
    PCT Pub. Date: Jul. 26, 1990
[30] Foreign Application Priority Data
    Jan. 19, 1989 [JP] Japan .................................. 1-8733
[51] Int. Cl.$^5$ ................................................ G01N 21/90
[52] U.S. Cl. ................................ 356/240; 250/223 B
[58] Field of Search .................... 356/239, 240, 250; 250/223 B; 358/106

[56] References Cited

U.S. PATENT DOCUMENTS

| | | | |
|---|---|---|---|
| 4,368,980 | 1/1983 | Aldred et al. | 356/240 |
| 4,428,674 | 1/1984 | Giebel et al. | 356/240 |
| 4,448,526 | 5/1984 | Miyazawa | 250/223 B |
| 4,606,635 | 8/1986 | Miyazawa et al. | 356/240 |

FOREIGN PATENT DOCUMENTS

88/00862 2/1988 World Int. Prop. O. .

Primary Examiner—Vincent P. McGraw
Attorney, Agent, or Firm—Birch, Stewart, Kolasch & Birch

[57] ABSTRACT

A method for discriminating recovered beverage containers (10) is provided. The method comprises the steps of selecting any particular color according to the color of the beverage contained in the container (10), measuring the area of the selected color in the container (10), determining whether the measured area of the color is within the fixed range or not, and discriminating the beverage containers (10) in accordance with the determined result.

6 Claims, 3 Drawing Sheets

METHOD FOR DISTINGUISHING BETWEEN RECOVERED CONTAINERS FOR THE PRESENCE OR ABSENCE OF CONTAMINANTS

TECHNICAL FIELD

The present invention relates to a method for inspecting recovered beverage containers. More specifically, the invention is concerned with a method for distinguishing and sorting beverage containers for further cleaning and/or use by optically identifying the beverage residue in the recovered containers.

BACKGROUND ART

Systems for vending beverages such as cola, juice, beer, etc. is roughly classified into two types.

The first type is a system in which used containers are not recovered. In general, this is called as one-way system. According to this system, for instance, beverages are filled in cans at a factory, being transported to an automatic vending machine and consumed by the consumer. The can containing the beverage is not recovered and is thereafter discarded by him.

The second type is a system in which used containers are recovered and which can be called as two-way system. In this system, for instance, beverages are bottled at a factory, being transported to an automatic vending machine and consumed by the consumer. The bottles containing the beverages are recovered for re-use.

The one-way system is generally convenient and has been widely employed as a preferable system. Recently, however, there is a strong voice demanding that two-way system should be adopted in view of the economical efficiency of reusing bottles or the effective use of an automobile transporting such beverages.

An important problem in the two-way system is what kind of inspection and washing should be conducted in order to obtain containers for re-use.

Hitherto, the following procedure has been adopted, for example, i.e. recovered containers are visually inspected by a human and the containers considered uncleanable are removed and only the good containers are washed.

Such human inspection is an operation which is simple but requires him to be under a great amount of tension. Therefore, its mechanization has been demanded.

In contrast, the following inspection has been suggested, i.e. an inspection by which the beverage residue in the recovered container is withdrawn and then the residue is analyzed by means of an analyzer. However, since the inspection using such analyzer takes much time and is costly, this is not efficient.

DISCLOSURE OF THE INVENTION

Thanks to an advanced washing technique, even if various types of foreign materials have remained in the bottle, these materials do not substantially remain after washing the bottle, thereby permitting the bottle to be used again as a beverage container.

However, if tempura oil or the like remains as foreign matter in the bottle, this involves a problem of adhering to a brush of the washer and causing a trouble in later washing.

Therefore, the following operation has been suggested, i.e. an operation in which the recovered bottles are distinguished by determining whether they are bottles considered to have been recovered without being truly utilized for other purposes or whether they are bottles considered to have been utilized for other purposes and thereafter, the bottles recovered without being used for other purposes are washed in accordance with an usual washing step, while the bottles determined to have been used for other purposes are washed in accordance with a different washing step. Such washing system is judged to have improved efficiency and to be preferable.

In the case of employing such a washing system, it becomes an important problem how the recovered bottles are distinguished by determining whether they are bottles considered to have been recovered without being truly utilized for other purposes or whether they are bottles considered to have been used for other purposes.

On the other hand, in a beverage container having a screwed cap the consumer desires to cap the container after drinking the beverage for the purpose of protecting the mouth of a bottle, etc. Because of this, this type of capped container is returned to the factory in a high proportion. Usually, some amount of beverage residue remains in the bottle even after the beverage is poured into a cup or the like. If the bottle is capped after drinking the beverage as above, evaporation of the beverage is inhibited. For instance, 2 cc or more of cola generally remains in a returned one-liter Coca-Cola bottle.

Even in the case of a container not using a screw cap, dried beverage matter adheres as residue to the bottom of the container.

On the contrary, where the bottle has been utilized for other purposes, there is no possibility that beverage residue remains at the bottom of the bottle.

Accordingly, recovered bottles can be distinguished as to whether they are bottles considered to have been used for other purposes or not by detecting whether some of the beverage remains at the bottom of the recovered bottle.

According to the present invention, there is provided a method for inspecting recovered beverage containers which comprises the steps of selecting any particular color according to the color of beverage contained in the container, measuring the area of the selected color in the container, determining whether the area of the selected color is within a fixed range, and distinguishing and sorting the beverage containers in accordance with the determined result.

In the method for discriminating the recovered beverage containers according to the present invention, a specific color is chosen on the basis of the color of the beverage residue contained in the container. For instance, the color of the beverage itself, the beverage color recognized through the container, the color recognized when the beverage gets dry, etc. is chosen.

The area of the selected color in the container is then measured. It is then determined whether the measured color area falls into a fixed range or not. If the measured area of the color is within the fixed range, its container is judged not to have been utilized for other purposes. And if the area is outside the fixed range, its container is judged to have been used for other purposes.

The beverage containers are discriminating according to whether the measured color area falls into this scope or not.

BEST MODE FOR CARRYING OUT THE INVENTION

Next, by referring to the accompanying drawings an explanation will be about the inspection apparatus for implementing the process for distinguishing between and sorting recovered containers in accordance with preferable working example of the present invention.

Figure 1:
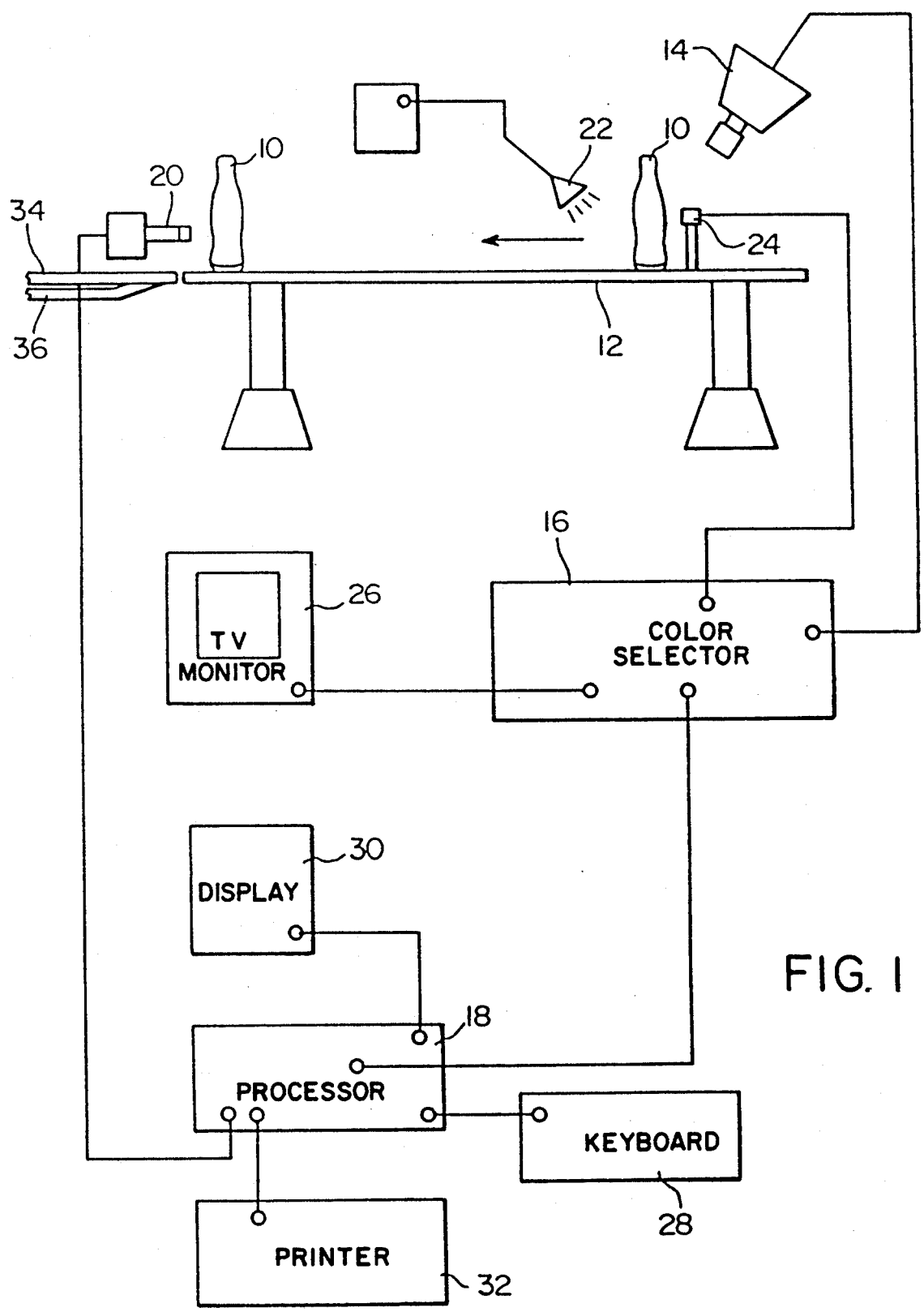
FIG. 1 is a sketch of the discrimination device for working the recovered bottle discrimination method according to one working example of the present invention.

As shown in FIG. 1, this inspecting apparatus is provided with a conveyor unit 12 for moving the recovered bottle 10 continuously, a camera unit 14, a color selector 16, an information processor unit 18 and a bottle rejector 20.

The conveyor unit 12 operates to move the recovered bottle 10 continuously at a rate of 10 to 400 pcs/min., for example. There is mounted an illuminator unit 22 for illuminating the bottle 10 in the fixed position on the conveyor unit 12.

On the conveyor unit 12 there is further installed a bottle sensor 24. A detection signal from a bottle sensor 24 is fed to the color selector 16 when the bottle 10 has reached the fixed position.

The camera unit 14 is connected to the color selector 16. Depending on the detection signal from the bottle sensor 24, one picture is taken per bottle, for instance. In the illustrated example the camera unit 14 takes a slant picture of the bottle. When desirable, the camera unit can be so arranged as to take a picture of the bottle immediately from the top. By taking such picture of the bottle immediately from the top, the present invention can be also applied to an opaque container. As the camera unit 14 can be used a solid state video camera unit which uses a CCD having 250,000 pixels, for instance.

The color selector 16 is further connected to a monitor TV set 26 and an image taken by the camera unit 14 is displayed on the screen of the monitor TV set 26.

Moreover, the color selector 16 stores any color selected depending on the color of the beverage, the beverage color observed through the container or the color recognized when the beverage gets dry, etc. beforehand. On the screen of the monitor TV set 26 can be displayed only the selected color portion of the picture taken by the camera unit 14, and sent to the color selector 16. A currently available color selector can specify a color with sufficient precision. Where a particular color e.g. cola is selected, a liquid having any other color will not be displayed. Where particular cola color is substantially present in the picture generated, the picture displayed on the screen of the monitor TV set 26 is the same as that in the case of an empty bottle.

In addition, the color selector 16 counts the number of pixels of color on the picture taken by the camera unit 14 detecting the above selected color and emits the counted number as an output. This pixel number corresponds to the area of the selected color in the taken picture.

An information processor unit 18 stores a desired range of the pixel number inputted by a key board 28 an input/output means, e.g. a range of the pixel number of 60 to 60,000. Being 60 or less in the pixel number means that only the slight amount of beverage remains at the bottom of the container or absolutely no beverage residue is found at the container bottom. Accordingly its container is determined to have been utilized for other purposes. Being 100,000 or more in the pixel number indicates, that the selected color has been detected in a pixel number greater than that detected where the container is filled with the beverage. This indicates that trouble has occurred. These ranges can be selected according to various conditions. For instance, they can be chosen variously by the kind of camera unit, used relative position between the camera unit and the bottle, shape and transparency of the bottle.

The information processor unit 18 is connected to the color selector 16. Thus unit 18 receives the pixel number detected from the selected color in the taken picture and outputted from the color selector 16, determines whether this pixel number falls within the stored desirable range of the pixel number emits its results as an output.

The information processor unit 18 is further, connected to a display monitor 30 and a printer 32 for displaying data of the above pixel number in a plurality of pictures for a series of the bottles 10.

The bottle rejector 20 is also connected to the information processor unit 18 and works and operates to sort and bottle 10 to either a first course 34 or a second course 36.

Thus, the bottle 10 guided to the first course 34 means being a bottle in which the pixel number within the desired range has the selected color in these pictures. This indicates that the residue having a fixed color is present in this bottle 10 in a predetermined amount. While, the bottle 10 guided to the second course 36 means being a bottle in which the residue with any fixed color is not present in a predetermined amount.

Next, by referring to FIGS. 2 to 5 an explanation will be made with respect to one liter size Coca-Cola bottles.

Figure 2A:
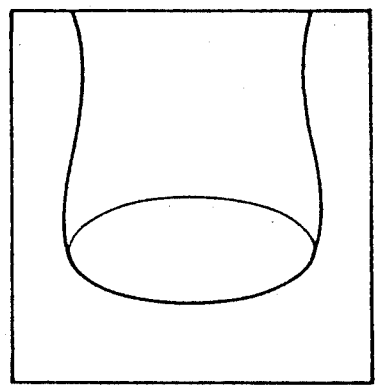
FIGS. 2-(a) and 2-(b) are a picture on the screen of the monitor TV set indicating an usual image of the bottle having totally no residue and a picture showing only the selected color portion of this bottle, respectively.
Figure 2B:
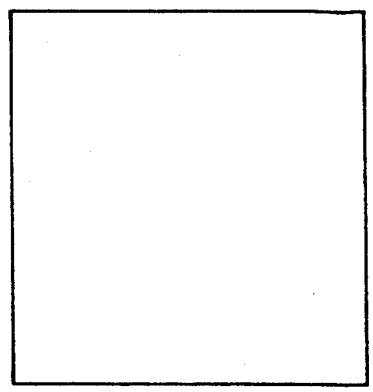

FIG. 2-(a) is a picture on the screen of the monitor TV set 26 indicating a normal image of the bottle in which absolutely no residue is found. FIG. 2-(b) is a picture showing only the portion of the selected color of this bottle. In this case, no selected color portion is found and the pixel number detecting the selected color is zero.

Figure 3A:
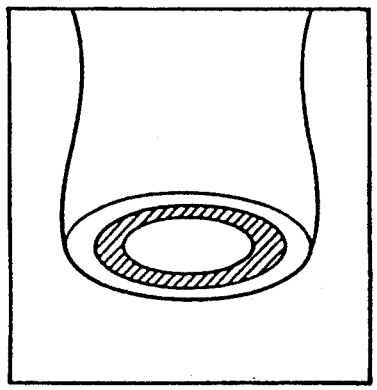
FIGS. 3-(a) and 3-(b) are a picture on the screen of the monitor TV set indicating an usual image of the bottle in which 2 cc of the residue remains and a picture showing only the selected color portion of this bottle, respectively.
Figure 3B:
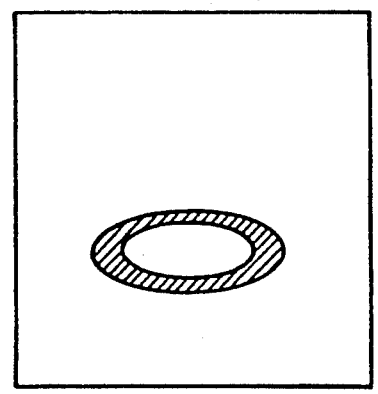

FIG. 3-(a) is a picture on the screen of the monitor TV set 26 indicating a typical image of a bottle in which a typical quantity of the residue, e.g. 2 cc remains. FIG. 3-(b) is a picture showing only the portion of the selected color of this bottle. In this case, the pixel number detected of the selected color is for example 80-100.

Figure 4A:
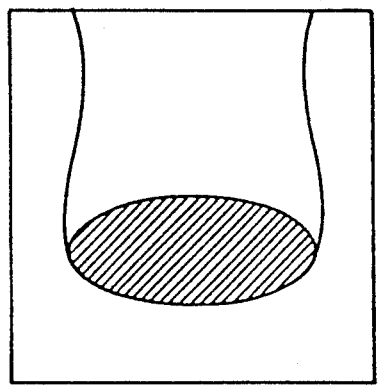
FIGS. 4-(a) and 4-(b) are a picture on the screen of the monitor TV set indicating an usual image of the bottle in which 20 cc of the residue remains and a picture showing only the selected color portion of this bottle, respectively.
Figure 4B:
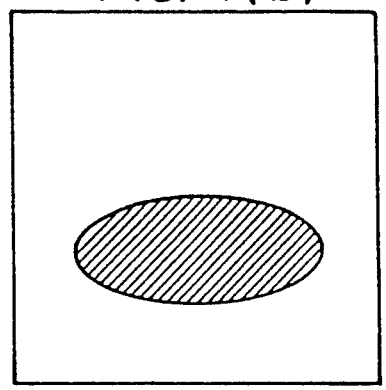

FIG. 4-(a) is a picture on the screen of the monitor TV set 26 indicating a typical image of the bottle in which the quantity of the residue is relatively large, e.g. 20 cc remains. FIG. 4-(b) is a picture showing only the portion of the selected color of this bottle. In this case, the pixel number detected of the selected color is for example 8,000-10,000.

Figure 5A:
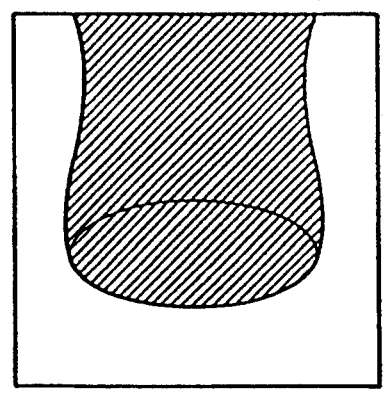
FIGS. 5-(a) and 5-(b) are a picture on the screen of the monitor TV set indicating an usual image of the bottle in which 800 cc of the residue remains and a picture showing only the selected color portion of this bottle, respectively.
Figure 5B:
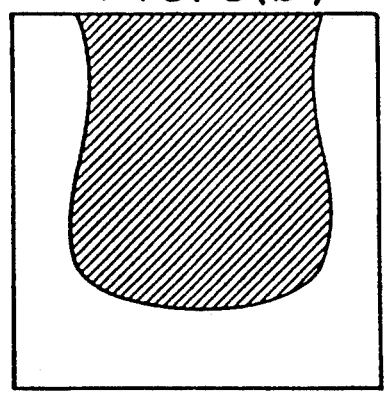

FIG. 5-(a) is a picture on the screen of the monitor TV set 26 indicating a typical image of the bottle in which the beverage is hardly consumed and therefore, a large amount of the residue remains, for example, 800 cc of the residue remains. In this case, the pixel number detecting the selected color is for example, 40,000-50,000.

As shown in the above example, where the desired range of the stored pixel number is 60-10,000, the bottle shown in FIG. 2 is guided to the second course 36 by means of the bottle rejector 20, while the bottles shown in FIGS. 2 to 5 are guided to the first course 34.

Thus, it is possible to distinguish which of the bottles recovered have not been used for other purposes from those which have been utilized for other purposes.

Further, in the above example, the explanation was made by considering, as an example, a container which uses a screw cap. But the present invention can be also applied to a container not using a screw cap.

In this case, since the container is uncapped, the beverage residue remaining in the container has dried up, and the dry beverage matter adheres to the bottom of the recovered container.

By measuring the color and the area at the bottom of the container to which the dry beverage matter adheres it is possible to discriminate bottles recovered without being used for other purposes from those utilized for other purposes.

Or the above selection is possible by adding a small amount of water of the like to the bottle after being recovered to thereby to reproduce the beverage and then measuring the color and the area of the reproduced beverage as described above.

Further, in a situation wherein some of the recovered plural containers have some amount of undried liquid beverage residue at the bottom and others have some amount of dried beverage matter at the bottom, the present invention can be so constructed that two colors or more are selected and any preferable range of areas occupied by these colors can be decided beforehand and the recovered bottles are judged to be those recovered without being used for other purposes where they agree to any one of conditions for the range of respective color areas.

Accordingly to the present invention, it is possible to precisely distinguish between which of the bottles recovered used for other purposes and those which have been utilized for other purposes. Further, the bottles can be washed more efficiently.

I claim:

1. A method for inspecting recovered beverage containers and for distinguishing containers with beverage residue therein from containers with contaminates therein which comprises the steps of:

selecting and storing a predetermined color corresponding to the color of the beverage residue in the container, measuring the area of the selected color of beverage residue in a bottom region of the container, determining whether or not the size of the measured area of the color representing beverage residue is within a predetermined range, and distinguishing the beverage containers in accordance with the results of the determining step, the presence of a measured area of the color of the beverage residue within said predetermined range indicating the absence of contaminates within a container.

2. The method according to claim 1 wherein the step of measuring the area of the selected color of beverage residue is made by counting the number of pixels in a picture generated by a camera unit detecting the selected color.

3. The method according to claim 1 or 2 wherein a fixed amount of water is supplied into the container before measuring the size of the area of the selected beverage residue color.

4. The method according to claim 2 where said camera unit comprises a video camera.

5. The method according to claim 2, wherein said determining step comprises the additional steps of:

entering and storing a pixel number count in a processor for establishing said range;

feeding the selected color to the processor, and comparing the number of pixels counted of said selected color during said measuring step against the stored pixel number count in said processor.

6. The method according to claim 5, wherein said distinguishing step further includes the step of sorting the beverage containers in accordance with the results of the determining step.

* * * * *